United States Patent [19]

Li

[11] Patent Number: 4,946,468
[45] Date of Patent: Aug. 7, 1990

[54] SUTURE ANCHOR AND SUTURE ANCHOR INSTALLATION TOOL

[75] Inventor: Lehmann K. Li, Wellesley, Mass.

[73] Assignee: Mitek Surgical Products, Inc., Norwood, Mass.

[21] Appl. No.: 449,118

[22] Filed: Dec. 8, 1989

Related U.S. Application Data

[63] Continuation of Ser. No. 362,004, Jun. 6, 1989, abandoned.

[51] Int. Cl.[5] .............................................. A61B 17/00
[52] U.S. Cl. ..................................... 606/232; 606/72; 606/75; 606/78
[58] Field of Search ............................. 606/232, 72–78

[56] References Cited

U.S. PATENT DOCUMENTS

| | | | |
|---|---|---|---|
| 3,699,969 | 10/1972 | Allen | 128/330 |
| 3,716,058 | 2/1973 | Tanner, Jr. | 128/337 |
| 4,245,545 | 1/1981 | Freeman | 411/342 |
| 4,573,844 | 3/1986 | Smith | 411/340 |
| 4,669,473 | 6/1987 | Richards et al. | 128/334 C |
| 4,741,330 | 3/1988 | Hayhurst | 128/92 YF |

*Primary Examiner*—Randall L. Green
*Assistant Examiner*—Gary Jackson
*Attorney, Agent, or Firm*—Schiller, Pandiscio & Kusmer

[57] ABSTRACT

A new and improved suture anchor of the sort adapted to anchor an intermediate portion of a piece of conventional suture in bone, and a new and improved installation tool for deploying the same, said installation tool being adapted to releasably hold at least one curved needle which is attached to said piece of conventional suture.

55 Claims, 7 Drawing Sheets

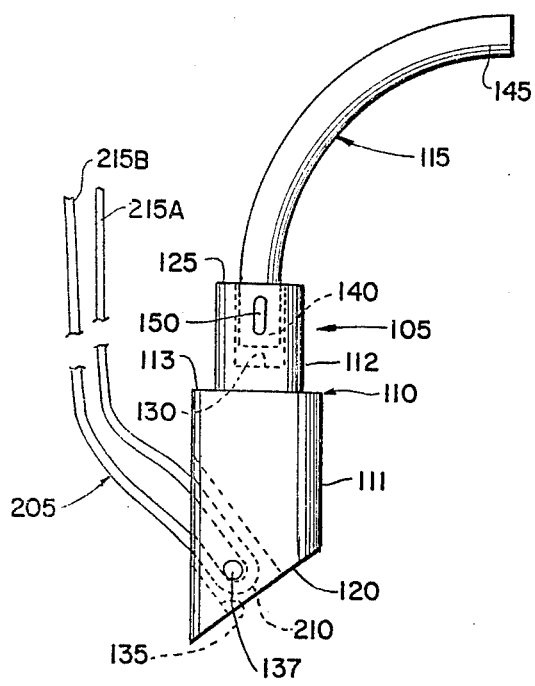
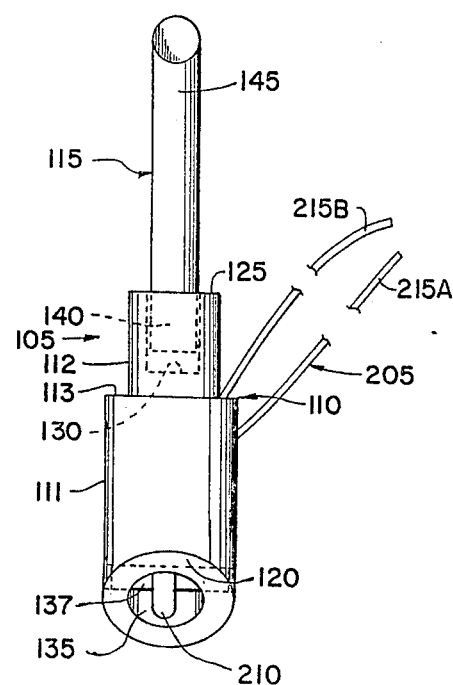
Fig. 1
Fig. 2

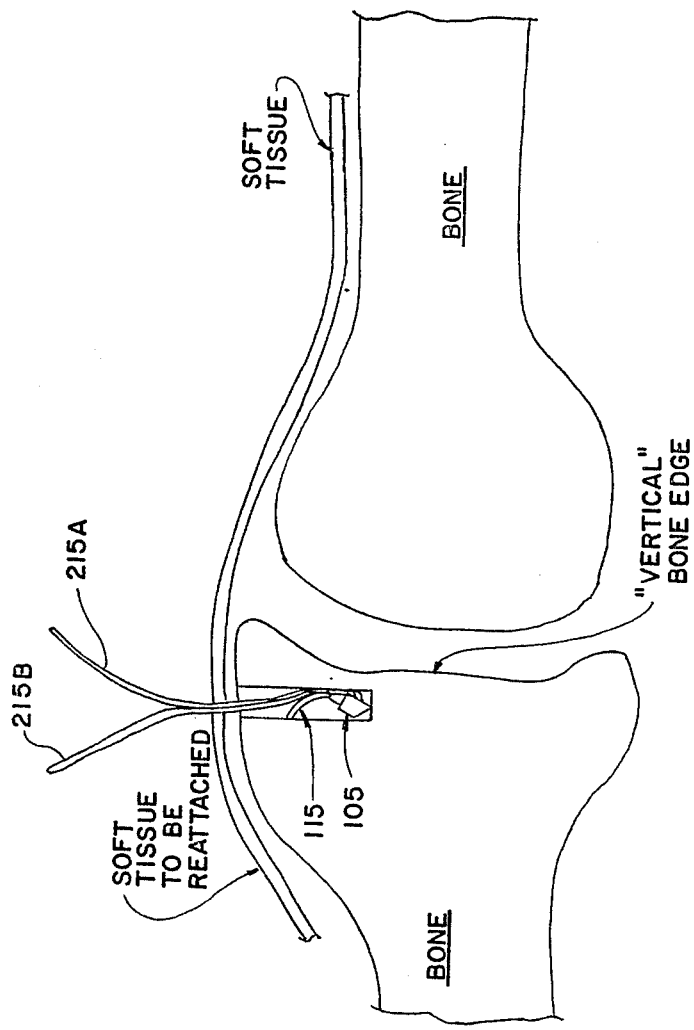

SUTURE ANCHOR AND SUTURE ANCHOR INSTALLATION TOOL

This application is a continuation of application Ser. No. 07/362,004 filed Jun. 6, 1989, now abandoned.

FIELD OF THE INVENTION

This invention relates to surgical devices in general, and more particularly to suture anchors of the sort adapted to anchor one portion of a piece of conventional suture in bone, and installation tools for deploying the same.

BACKGROUND OF THE INVENTION

Numerous devices are currently available to attach objects to bone. More specifically, screws, staples, cement and sutures have all been used to attach soft tissue (e.g. ligaments, tendons, muscles, etc.), bone and inanimate objects (e.g. prostheses) to bone.

In certain situations it is desirable to anchor one end of a piece of conventional suture in bone, leaving the other end of the piece of suture residing free outside the bone so that the free end of the suture can then be used to attach the desired object (e.g. a ligament or prosthesis) to the bone.

Suture anchors for anchoring one end of a piece of conventional suture in bone, and installation tools for deploying the same, are described and illustrated in pending U.S. patent application Ser. No. 051,367, filed 5/18/87 by Roland F. Gatturna et al. for "Suture Anchor", pending U.S. patent application Ser. No. 132,940, filed 12/15/87 by James E. Nicholson et al. for "Suture Anchor Installation Tool", and pending U.S. patent application Ser. No. 308,318, filed 2/8/89 by Roland F. Gatturna.

Still other suture anchors and suture anchor installation tools are described and illustrated in U.S. Pat. No. 4,632,100, issued 12/30/86 to Somers et al., U.S. Pat. No. 4,738,255, issued 4/19/88 to Goble et al., and U.S. Pat. No. 4,741,330, issued 5/3/88 to Hayhurst.

In certain circumstances it may be desirable to have more than one suture end residing free outside the bone for use in attaching the desired object or objects to the bone. In this situation, with the suture anchors of the above-identified pending U.S. Pat. applications Ser. Nos. 051,367 and 132,940, as well as with the suture anchors of the above-identified U.S. Pat. Nos. 4,632,100, 4,738,255 and 4,741,330, the only recourse is to implant more than one suture anchor to provide the desired more than one free suture ends. This technique can have obvious disadvantages.

The above-identified U.S. patent application Ser. No. 308,318 discloses a suture anchor wherein two separate sutures are attached to a single suture anchor, thereby yielding two free suture ends for each suture anchor deployed, but this arrangement requires that two separate sutures be threaded through the anchor's suture-receiving bore and thereafter tied to one another so as to affix the two separate sutures to the suture anchor. This threading and tying operation can be relatively time-consuming to achieve. In addition, this attachment technique creates the additional risk that the sutures can become separated from the suture anchor if the knot should fail.

OBJECTS OF THE INVENTION

The principal objects of the present invention are to provide a new and improved suture anchor, and a new and improved suture anchor installation tool.

Another object of the present invention is to provide a new and improved suture anchor of the sort adapted to anchor an intermediate portion of a piece of conventional suture in bone, thereby leaving the two ends of the suture residing free outside the bone so that each of the free ends can then be used to attach the desired object or objects to the bone.

Still another object of the present invention is to provide a new and improved suture anchor of the sort adapted to anchor an intermediate portion of a piece of conventional suture in bone, thereby leaving the two ends of the suture residing free outside the bone so that each of the free ends can then be used to attach the desired object or objects to the bone, wherein the suture anchor is adapted to have the intermediate portion of the suture attached to the suture anchor without the tying of any knots in the suture.

SUMMARY OF THE INVENTION

These and other objects of the invention are achieved through the use of a novel suture anchor which comprises (a) a coupling member having a first end portion and a reduced second end portion, and a shoulder formed at the junction of the first end portion and the reduced second end portion, (b) at least one barb, the barb having a first end and a second end and being curved in its normal unstressed state and being capable of being elastically deformed to a substantially straight configuration, the barb being attached to the coupling member so that the second end of the barb is substantially displaced from the coupling member when the barb is in its normal unstressed state but is capable of being aligned with the coupling member when the barb is deformed to a substantially straight length, and (c) attachment means for attaching an intermediate portion of a piece of conventional suture to the suture anchor, the attachment means comprising a bore formed in the coupling member and a pin extending across the bore, whereby the suture can be passed around the pin so that an intermediate portion of the suture is supported by the pin and the two ends of the suture are free to attach the desired object or objects to bone when the suture anchor is deployed in the bone.

The foregoing suture anchor is used with a novel suture anchor installation tool which comprises a first body portion and a second body portion, the first body portion having a first end and a second end, the first end of the first body portion being hollow and having a slot extending from the first end of the first body portion towards the second end of the first body portion, the first end of the first body portion being sized to accommodate the reduced second end portion of the suture anchor and the slot being sized to accommodate the barb of the suture anchor, and the second body portion of the suture anchor installation tool having a first end and a second end, the second body portion having a hollow interior and an opening leading to the hollow interior, and the second body portion having a pair of grooves formed in its outer surface and sized to accommodate a pair of surgical needles, with the second end of the first body portion being joined to the first end of the second body portion, whereby the suture anchor may be attached to the suture anchor installation tool by fitting the reduced second end portion of the suture anchor into the first end of the first body portion of the installation tool and by fitting the barb of the suture anchor into the slot of the first body portion of the installation tool so that the barb extends upward and away from the first end of the first body portion of the installation tool, through the slot, with the shoulder of the suture anchor engaging the first end of the first body portion of the installation tool, and a suture attached to the suture anchor by passing a first intermediate portion of the suture around the suture anchor's pin may have a second intermediate portion of the suture stored inside the hollow interior of the second body portion, with needles attached to the two free ends of the suture being received in the pair of grooves formed in the outer surface of the second body portion of the installation tool.

BRIEF DESCRIPTION OF THE DRAWINGS

Still other objects and features of the present invention will be more fully described or rendered obvious in the following detailed description of the invention, which is to be considered together with the accompanying drawings wherein like numbers refer to like parts and further wherein:

FIG. 1 is a side view in elevation showing one side of a suture anchor formed in accordance with the present invention;

FIG. 2 is a side view in elevation showing another side of the suture anchor shown in FIG. 1, the suture anchor shown in FIG. 2 having been rotated 90 degrees from the position shown in FIG. 1;

FIG. 12A shows a typical situation in which a suture anchor is used to reattach soft tissue to bone;

DETAILED DESCRIPTION OF THE INVENTION

Figure 3:
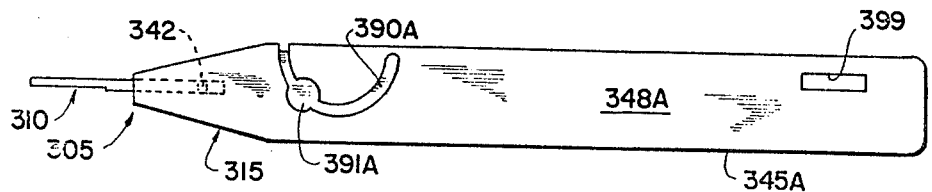
FIG. 3 is a side view in elevation showing the left side of a suture anchor installation tool formed in accordance with the present invention.

Looking first at FIGS. 1 and 2, there is shown a suture anchor 105 formed in accordance with the present invention. Suture anchor 105 generally comprises a coupling member 110 and a barb 115.

Coupling member 110 comprises a piece of 6AL4V titanium alloy having a cylindrical lower portion 111 and a cylindrical upper portion 112. Cylindrical lower portion 111 has a diameter which is greater than the diameter of cylindrical upper portion 112, whereby a shoulder 113 is formed at the junction of the coupling member's lower portion 111 and its upper portion 112. Coupling member 110 has a first end surface 120 disposed at one end of lower portion 111 and a second end surface 125 disposed at the opposite end of upper portion 112. First end surface 120 is disposed at an angle of approximately 30 degrees to the coupling member's longitudinal axis, and second end surface 125 is disposed at a right angle to the coupling member's longitudinal axis, as shown. The coupling member's upper portion 112 has a blind hole 130 opening on second end surface 125, and the coupling member's lower portion 111 has a bore 135 extending at an angle between the coupling member's side wall and its bottom end surface 120, as shown. Bore 135 extends at a right angle to the coupling member's bottom end surface 120. A pin 137 is mounted to opposing side walls of the coupling member near bottom end surface 120 so that the pin extends across the middle of bore 135, as shown.

Barb 115 comprises a curved length of nickel titanium alloy having a first end 140 and a second end 145. Barb 115 comprises an arc of approximately 120 degrees. Barb 115 is attached to the coupling member by fitting the barb's first end 140 in the coupling member's blind hole 130, whereby the barb's second end 145 extends upward and outward from the coupling member. The coupling member's upper portion 112 is then crimped inward at one or more points as shown at 150 (FIG. 1) to lock barb 115 to the coupling member. Barb 115 is made of such a nickel titanium alloy that it is capable of being elastically deformed to a substantially straight length when desired (i.e., so that the barb's second end 145 is aligned with its first end 140, as well as with the opposite end surfaces 120 and 125 of the coupling member). By way of example, barb 115 may be made out of binary nitinol such as that sold by Raychem Corporation of Menlo Park, California and Furukawa of Japan, or it might be made out of ternary nitinol such as that sold by Raychem Corporation and described in U.S. Pat. No. 4,505,767, issued 3/19/85 to Quinn. It is noted that the transition temperature of the nitinol must be below normal body temperature, such that the arc is substantially transitioned into the martensite state and exhibits elastic behavior on insertion into bone.

Still looking at FIGS. 1 and 2, a suture 205 having an intermediate portion 210 and opposite ends 215A, 215B is attached to suture anchor 105 by threading the suture around anchor pin 137 so that the intermediate portion 210 of the suture is supported by anchor pin 137 while the two ends 215A, 215B of the suture are left free of the suture anchor so that they may be used to attach the desired object or objects to bone when the suture anchor is deployed in the bone. Preferably the dimensions of the suture anchor's bore 135 and pin 137 are coordinated with the dimensions of suture 205 so that the suture may be easily threaded around pin 137 and yet will be snugly received in the suture anchor when it is threaded around anchor pin 137, so that the suture will remain in place relative to the suture anchor.

Looking next at FIGS. 3–8, there is shown a suture anchor installation tool 305 formed in accordance with the present invention. Suture anchor installation tool 305 generally comprises a cannula 310 and a handle 315.

Figure 6:
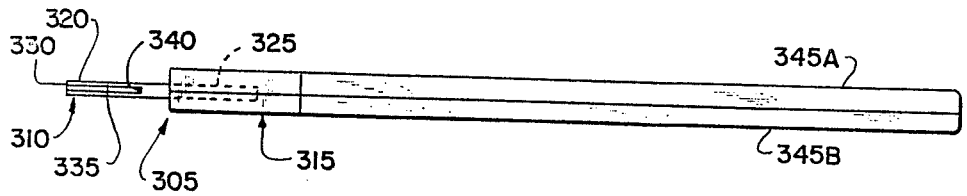
FIG. 6 is a bottom view showing the bottom side of the suture anchor installation tool shown in FIG. 3.
Figure 7:
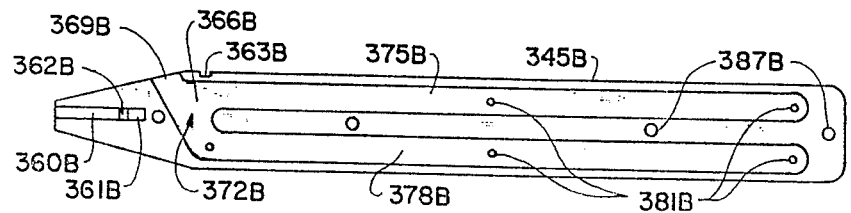
FIG. 7 is a side view in elevation showing the interior configuration of the right half of the suture anchor installation tool shown in FIG. 3.
Figure 8:
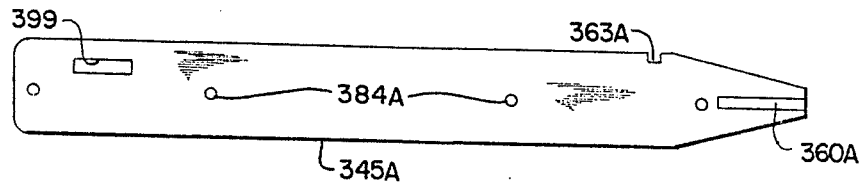
FIG. 8 is a side view in elevation showing the interior configuration of the left half of the suture anchor installation tool shown in FIG. 3.

As best seen in FIGS. 3 and 6, cannula 310 comprises a first end 320 and a second end 325. First end 320 terminates in a front end surface 330. Cannula 310 is hollow and has a longitudinally-extending front slot 335 (FIG. 6) formed in its side wall. Front slot 335 begins at front end surface 330 and terminates in a rear end surface 340. Cannula 310 also has a smaller opening 342 (FIG. 3) formed in its side wall at its rear end 325. Opening 342 is disposed 90 degrees from front slot 335, for reasons which will hereinafter be made clear.

Suture anchor installation tool 305 is intended to be used to install the suture anchor 105 previously described, and to this end the dimensions of cannula 310 are coordinated with the dimensions of suture anchor 105. More specifically, cannula 310 is sized relative to suture anchor 105 so that (a) the first end 320 of cannula 310 has an outer diameter which is smaller than, equal to or just slightly larger than the outer diameter of the suture anchor's lower portion 111, so that the smallest possible hole may be formed in the bone which is to receive the bone anchor, (b) the first end 320 of cannula 310 has an internal diameter which is slightly larger than the outer diameter of the suture anchor's upper portion 112, but slightly smaller than the outer diameter of the suture anchor's lower portion 111, whereby the suture anchor's upper portion 112 may be snugly received in the interior of cannula 310 but the suture anchor's lower portion 111 may not, with the cannula's front end surface 330 engaging the suture anchor's shoulder 113, as will hereinafter be described in further detail, (c) the cannula's slot 335 has a width slightly larger than the diameter of the suture anchor's barb 115, so that the barb will fit between the walls of first end 320 which define slot 335, as will hereinafter be described in further detail, and (d) slot 335 has a length sufficient to accommodate the suture anchor's barb 115 when the barb is bent backwards into the cannula during deployment of the suture anchor, as will hereinafter be described in further detail.

Figure 4:
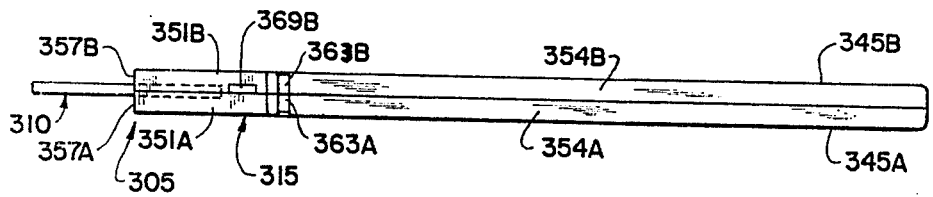
FIG. 4 is a top view showing the top side of the suture anchor installation tool shown in FIG. 3.
Figure 5:
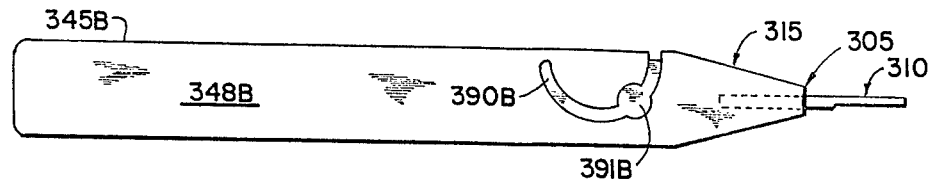
FIG. 5 is a side view in elevation showing the right side of the suture anchor installation tool shown in FIG. 3.

Still looking now at FIGS. 3–8, handle 315 comprises two members 345A, 345B which snap together in the manner shown to form a single handle unit having a left side surface 348A (FIG. 3), a right side surface 348B (FIG. 5), a pair of coplanar adjacent sloped surfaces 351A, 351B (FIG. 4), a pair of coplanar, adjacent top surfaces 354A, 354B (FIG. 4), and a pair of coplanar, adjacent front surfaces 357A, 357B (FIG. 4).

Member 345A is relieved at 360A (FIG. 8), and member 345B is relieved at 360B and at 361B so as to form a land 362B (FIG. 7), so that when the two members are joined together as will hereinafter be described in further detail, a blind hole type of interior chamber (hereinafter referred to as chamber 360A/360B) will be defined in the handle which opens on the two front surfaces 357A, 357B. Chamber 360A/360B is sized so as to receive the second end 325 of cannula 310, with the cannula's opening 342 receiving the land 362B, whereby cannula 310 and handle 315 can be attached to one another to function as a single unit, as will hereinafter be described in further detail.

Member 345A is also relieved at 363A (FIG. 8), and member 345B is relieved at 363B (FIG. 7), so that when the two members are joined together as will hereinafter be described in further detail, a surface groove (hereinafter referred to as groove 363A/363B) will be defined in the handle in top surfaces 354A, 354B (FIG. 4). Surface groove 363A/363B is formed so as to have a diameter somewhat larger than the diameter of a suture used with the installation tool, as will hereinafter be described in further detail.

Member 345B is also relieved at 366B (FIG. 7) so that when the two members are joined together as will hereinafter be described in further detail, an opening 369B (FIGS. 4 and 7) communicating with an interior chamber 372B (FIG. 7) will be formed, wherein opening 369B opens on sloped surface 351B (FIG. 4). More specifically, member 345B is relieved at 366B so that opening 369B is somewhat larger than four diameters of a suture being used with the tool, and so that a pair of parallel, elongated subchambers 375B, 378B are formed in the handle, with a plurality of dimples 381B rising slightly from the floor of each of the subchambers 375B, 378B. Inasmuch as chamber 372B serves to store an intermediate length of suture when a suture anchor is attached to the suture anchor installation tool, and inasmuch as dimples 381B serve to releasably hold the stored suture in place within the handle chamber, dimples 381B are sized so that at least two widths of suture can pass between each of the dimples and the surrounding wall of the subchambers, and dimples 381B are sized so that they rise only slightly above the floor of the subchambers so that the suture can slip over the top of the dimples during deployment, as will hereinafter be described in further detail.

Member 345A is also formed with a plurality of holes 384A (FIG. 8), and member 345B is also formed with a plurality of posts 387B (FIG. 7), whereby when it is desired to join handle member 345A to handle member 345B, the two members may be press fit together in the manner shown, with posts 387B seating in holes 384A, as will hereinafter be described in further detail.

Members 345A, 345B are also formed with curved surface grooves 390A, 390B in their side surfaces 348A, 348B (FIGS. 3 and 5), to receive and securely hold a pair of curved surgical needles therein, as will hereinafter be described in further detail. To this end, it will be appreciated that by forming surface grooves 390A, 390B with slightly smaller radii of curvature than the surgical needles which are to be held, and by squeezing the surgical needles slightly during insertion so as to reduce their radii of curvature, the surgical needles can be "spring loaded" into the grooves 390A, 390B so as to assure that the needles will be securely seated in the grooves. Surface grooves 390A, 390B include expanded portions 391A, 391B, as shown.

Member 345A also includes a horizontally elongated slot 399. Slot 399 is positioned to coincide with elongated subchamber 375B of member 345B, whereby access can be gained to the subchamber via slot 399, as will hereinafter be described in further detail.

Figure 9:
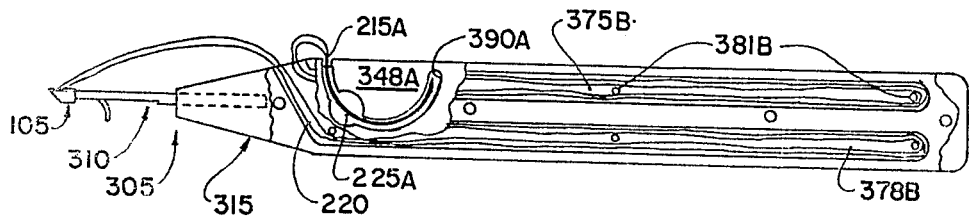
FIG. 9 is a side view in elevation, partially broken away, showing the suture anchor of FIGS. 1 and 2, with a suture attached, loaded into the suture anchor installation tool of FIGS. 3-8, the view being taken from the left side of the suture anchor installation tool.

Prior to using the foregoing apparatus in a surgical procedure, the apparatus is assembled as follows. First, a suture anchor 105, a suture 205, a cannula 310 and handle members 345A, 345B are assembled. Then the suture 205 having free ends 215A, 215B is attached to the suture anchor 105 by threading the suture around anchor pin 137 so that the intermediate portion 210 of the suture is supported by anchor pin 137 while the two ends 215A, 215B of the suture are left free of the suture anchor. Then suture anchor 105 is attached to the installation tool's cannula 310 by fitting the suture anchor's upper portion 112 into the front end of the cannula, with the cannula's front end surface 330 engaging the suture anchor's shoulder 113 and the suture anchor's barb 115 being accommodated in the cannula's slot 335. Next the rear end 325 of cannula 310 is positioned into the appropriate relieved portions of member 345B (i.e., the rear end 325 of the cannula is fit into housing chamber 360A/360B, with the cannula's rear opening 342 receiving handle land 362B, whereby the cannula's slot 335 will be oriented downward, 180 degrees away from the handle's top surfaces 354A, 354B). Next, an intermediate portion 220 of the suture is coiled into subchambers 375B, 378B around dimples 381B, with the suture doubling back on itself through opening 369B so as to leave the suture ends 215A, and 215B free outside handle 315, as shown in FIG. 9. Then members 345A and 345B are snapped together, so that suture anchor 105, cannula 310 and handle 315 will be united together as a single unit. Next surgical needles 225A, 225B (only one of which, 225A, is shown, in FIG. 9) are attached to the free ends 215A, 215B of the suture, and these needles are placed in the handle's surface slots 390A, 390B for storage therein until required. Then a crochet needle type of tool is inserted into slot 399 and manipulated so as to pull any excess outside suture back into the handle, and also so as to pull the suture taut within the handle.

Preferably, handle member 345A is formed out of a transparent plastic so that the suture contained inside the housing can be clearly observed during assembly and subsequent use.

The foregoing components may then be packaged, sterilized and stored until required during surgery.

Figure 10:
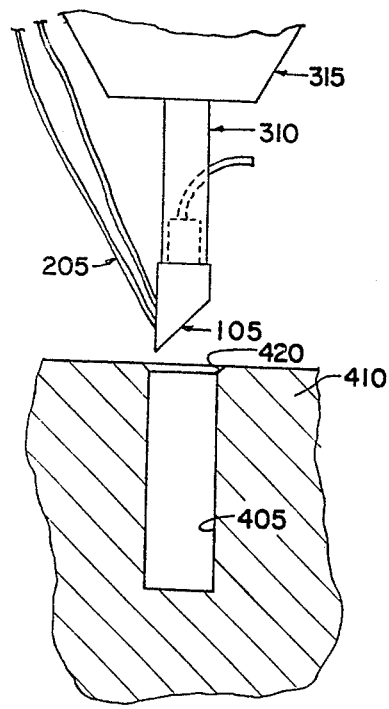
FIGS. 10-12 are a series of schematic views showing the suture anchor of FIGS. 1 and 2 being deployed into a bone hole using the suture anchor installation tool of FIGS. 3-8.
Figure 11:
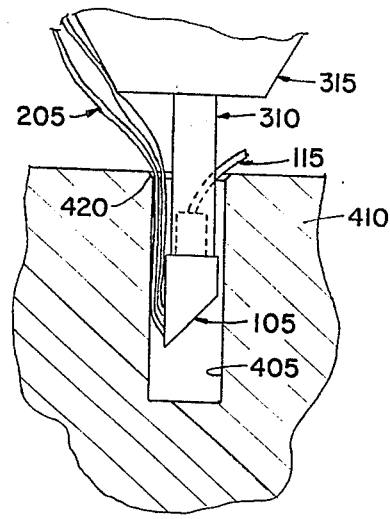
Figure 12:
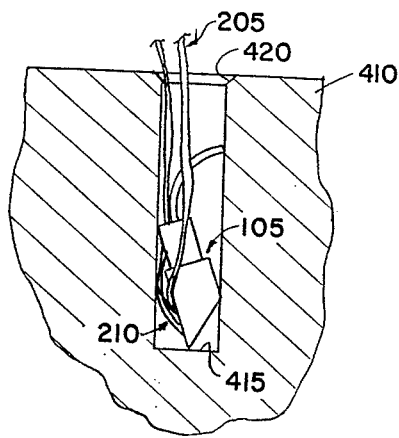

During surgery, the apparatus is used as follows. A hole 405 (FIG. 10) is first formed in a bone 410 which is to receive the suture anchor 115. As seen in FIGS. 10-12, bone 410 is preferably chamfered about the top end of hole 405 at 420 so as to eliminate any sharp surface which might cut the suture. Then the distal end of the suture anchor installation tool is pressed down into the predrilled hole 405 in bone 410 (FIGS. 10 and 11) until the leading tip of the suture anchor bottoms out on bone surface 415 (FIG. 12). As the distal end of the suture anchor installation tool forces the suture anchor down into the bone, the suture anchor's barb 115 engages the side wall of the bone, forcing the barb to retract inwards, into the cannula slot 335, so that the suture anchor and the cannula portion of the suture anchor installation tool can enter bone hole 405. As the suture anchor passes by the hard cortical outer portion of the bone and enters the softer cancellous interior region of the bone, the barb's resilient nature will cause it to bend itself back into a curved length, with the barb acting as a resilient hook to engage adjacent bone matter. When the suture anchor reaches the bone surface 415, the installation tool is withdrawn upward, whereupon engagement of the suture anchor's barb 115 with the surrounding bone causes the suture anchor to separate from the departing installation tool, so that the suture anchor remains securely anchored in position within the bone, keeping the intermediate portion 210 of suture 205 captured in place inside the bone. It is to be appreciated that as the retreating installation tool withdraws from the emplaced suture anchor, the superior mechanical strength and elasticity of barb 115 will cause the barb to attempt to return to its unstressed, curved state, and this action will kick the suture anchor sideways somewhat, as shown in FIG. 12, causing a multipoint engagement of the suture anchor with the surrounding walls of bone 410. This has the effect of consistently and reliably further securely anchoring the suture anchor in the bone.

It is also to be appreciated that as the retreating installation tool withdraws from bone hole 405 and thereby separates from the emplaced suture anchor, the intermediate portion 220 of the suture (previously stored within the interior of handle 315, as described above) will play out from the installation tool's cavity 372B via opening 369B. Thereafter the needles 225A, 225B (attached to the free ends 215A, 215B of the suture and securely mounted in handle slots 390A, 390B as noted above) are freed from the handle and used, in conjunction with the associated suture, to fasten the desired object or objects to the bone. It is to be appreciated that the expanded portions 391A, 391B of surface grooves 390A, 390B facilitate removal of the needles from the slots, by permitting forceps or another tool to grasp the needles and separate them from handle 315.

(It is, of course, to be noted that the device could be provided without needles being attached to the suture until the suture anchor and suture anchor installation tool are unpackaged in the operating room; if this is the case, the surgeon simply attaches the needles to the suture upon unpackaging.)

Preferably the installation tool's cannula 310 and handle 315 are sized and assembled so that the installation tool's front surfaces 357A, 357B will act as natural stop members to inhibit further penetration of the tool into bone 410, in the event that hole 405 is formed too deep in the bone.

It should also be appreciated that the construction of the present suture anchor installation tool provides the additional feature of the user always knowing the direction the barb extends in during deployment. More specifically, it will be appreciated that by virtue of the fact that the cannula's slot 335 always faces directly downward (i.e., directly away from the handle's top surfaces 354A, 354B), the user holding handle 315 will always know the orientation of the suture anchor's barb 115 relative to the suture anchor installation tool. Such a feature can be very important in situations where the suture anchor installation tool must set the suture anchor very close to a "vertical" bone edge, since in such situations the suture anchor should be deployed with its barb oriented directly away from the vertical bone edge so as to minimize any possibility the barb could project through the vertical bone edge (and hence extend out of the bone) during deployment. By way of illustration, FIG. 12A shows a typical situation in which soft tissue is being reattached to a bone with a suture anchor. In this situation it is desirable to place the suture anchor as close to the vertical bone edge as possible, so that the soft tissue being reattached can be reattached to the bone fairly close to the end of the bone. This necessitates placing the anchor-receiving bone hole fairly close to the vertical bone edge, so that the barb should be deployed so that it will spring away from the vertical bone edge during deployment and thereby avoid the possibility that the barb could poke through the vertical bone edge and into the joint as the barb returns to its curved orientation.

It should, of course, be appreciated that one or both of the suture anchor 105 and suture anchor installation tool 305 described above could be modified somewhat without departing from the scope of the present invention.

Thus, for example, suture anchor 105 could have its coupling member 110 formed out of a material other than 6AL4V titanium alloy, and its barb 115 formed out of a material other than nickel titanium alloy. By way of example, coupling member 110 could be formed out of titanium and its alloys, ceramics, plastics, stainless steel and other suitable bio-compatible materials. By way of further example, barb 115 could be formed out of titanium and its alloys, and stainless steel. Nitinol is currently the preferred material due to its superior elastic properties.

It is also anticipated that the installation tool's cannula 310 might be formed out of a cylindrical member which is hollow on its leading tip only, and which is solid on its trailing end. Of course, if this is the case, a different method for attaching the rear end 325 of cannula 310 to housing 315 must be used, since cannula opening 342 will no longer be available to mate with handle land 362B, as previously described. In this case cannula 310 might simply be glued to handle 315.

It is also anticipated that the suture anchor might be modified somewhat from the design shown in FIGS. 1 and 2 so that the suture anchor's coupling member comprises a body of singular diameter.

Figure 13:
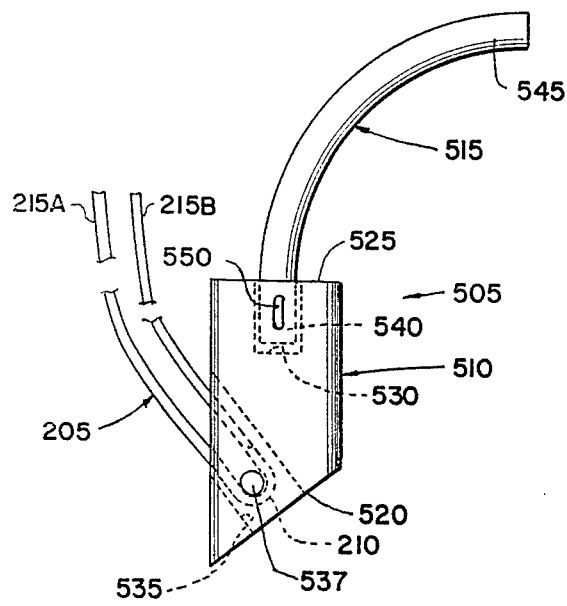
FIG. 13 is a side view in elevation showing one side of an alternative form of suture anchor formed in accordance with the present invention.
Figure 14:
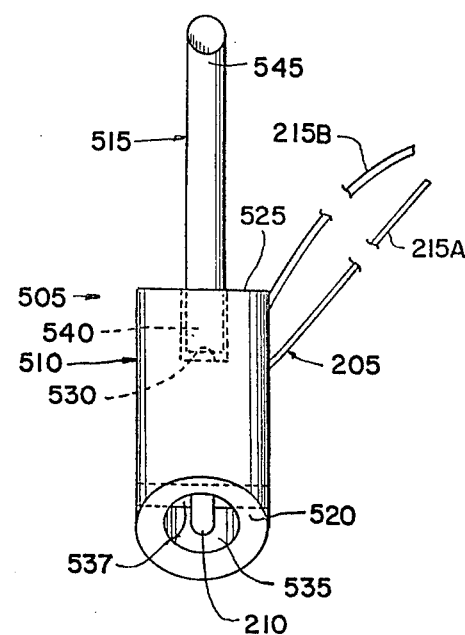
FIG. 14 is a side view in elevation showing another side of the suture anchor shown in FIG. 13, the suture anchor shown in FIG. 14 having been rotated 90 degrees from the position shown in FIG. 13.

More specifically, and looking now at FIGS. 13 and 14, there is shown a suture anchor 505 which generally comprises a coupling member 510 and a barb 515.

Coupling member 510 comprises a piece of 6AL4V titanium alloy having a cylindrical body characterized by a first end surface 520 and a second end surface 525 disposed at the opposite end of the coupling member. First end surface 120 is disposed at an angle of approximately 30 degrees to the coupling member's longitudinal axis, and second end surface 125 is disposed at a right angle to the coupling member's longitudinal axis, as shown. The coupling member has a blind hole 530 opening on second end surface 525, and the coupling member has a bore 535 extending at an angle between the coupling member's side wall and its bottom end surface 520, as shown. Bore 535 extends at a right angle to the coupling member's bottom end surface 520. A pin 537 is mounted to opposing side walls of the coupling member near bottom end surface 520 so that the pin extends across the middle of bore 535, as shown.

Barb 515 comprises a curved length of nickel titanium alloy having a first end 540 and a second end 545. Barb 515 comprises an arc of approximately 120 degrees. Barb 515 is attached to the coupling member by fitting the barb's first end 540 in the coupling member's blind hole 530, whereby the barb's second end 545 extends upward and outward from the coupling member. The coupling member's body is then crimped inward at one or more points as shown at 550 (FIG. 13) to lock barb 515 to the coupling member. Barb 515 is made of such a nickel titanium alloy that it is capable of being elastically deformed to a substantially straight length when desired (i.e., so that the barb's second end 545 is aligned with its first end 540, as well as with the opposite end surfaces 520 and 525 of the coupling member). By way of example, barb 515 may be made out of binary nitinol such as that sold by Raychem Corporation of Menlo Park, California and Furukawa of Japan, or it might be made out of ternary nitinol such as that sold by Raychem Corporation and described in U.S. Pat. No. 4,505,767, issued 3/19/85 to Quinn.

Still looking at FIGS. 13 and 14, a suture 205 having an intermediate portion 210 and opposite ends 215A, 215B is attached to suture anchor 505 by threading the suture around anchor pin 537 so that the intermediate portion 210 of the suture is supported by anchor pin 537 while the two ends 215A, 215B of the suture are left free of the suture anchor so that they may be used to attach the desired object or objects to bone when the suture anchor is deployed in the bone. Preferably the dimensions of the suture anchor's bore 535 and pin 537 are coordinated with the dimensions of suture 205 so that the suture may be easily threaded around pin 537 and yet will be snugly received in the suture anchor when it is threaded around anchor pin 537, so that the suture will remain in place relative to the suture anchor.

It will be appreciated that suture anchor installation tool 305 must be modified slightly to work in conjunction with the suture anchor 505 shown in FIGS. 13 and 14. More specifically, the design of the front end 320 of the installation tool's cannula 310 must be modified slightly from that shown in FIGS. 314 12 so that the cannula can mate with and properly support the modified form of suture anchor 505 shown in FIGS. 13 and 14 during deployment of the suture anchor.

Figure 15:
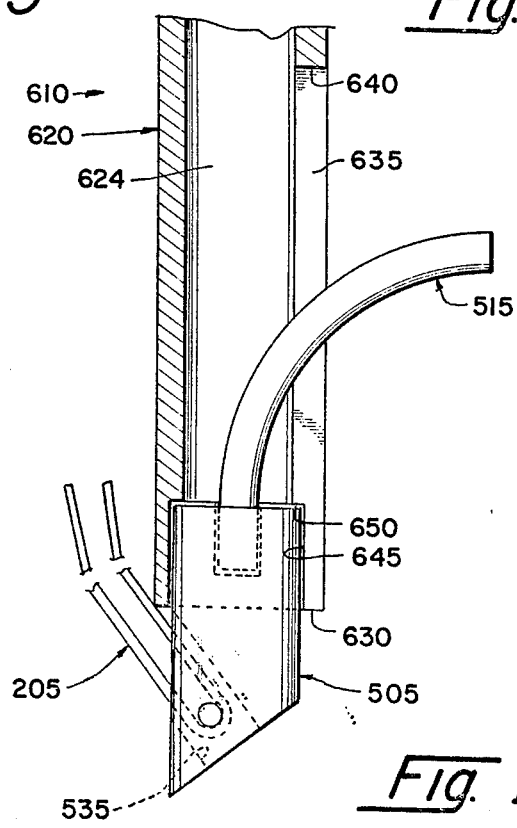
FIG. 15 is a partial side view in elevation showing the suture anchor of FIGS. 13 and 14, with a suture attached, loaded into a modified form of the suture anchor installation tool.

Looking next at FIG. 15, suture anchor 505 is shown in engagement with the front end 620 of a cannula 610 of an installation tool; only the front end 620 of the cannula is shown, inasmuch as the remainder of the cannula is identical to the rear end of the cannula 310 already described and illustrated. It will be appreciated that the unshown portion of cannula 610 mates with an installation tool handle 305 such as that already described and illustrated, in the manner already described and illustrated.

The front end 620 of cannula 610 is characterized by an internal bore 624 which has a diameter less than the diameter of the suture anchor's coupling member 510, and a counterbore 645 which opens on the cannula's distal end 630 and terminates in an internal shoulder 650. Counterbore 645 is sized to have a diameter slightly greater than the diameter of the suture anchor's coupling member 510, and shoulder 650 is positioned a sufficient distance from distal end 620 to allow a portion of the suture anchor's coupling member to be received within the cannula's counterbore 645, with the suture anchor's bore 535 still being completely exposed, as shown. A slot 635 terminating in a rear surface 640 is provided to accommodate the suture anchor's barb 515.

Except for the foregoing differences in construction, and except for the foregoing differences in the way coupling member 515 mates with cannula 610, it will be appreciated that suture anchor 505 and cannula 610 operate in substantially the same manner as suture anchor 105 and cannula 310 previously described.

Figure 16:
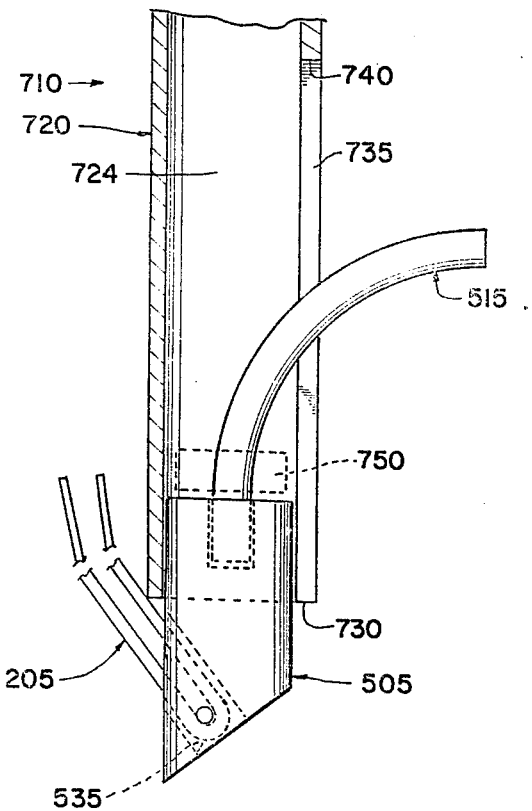
FIG. 16 is a partial side view in elevation showing the suture anchor of FIGS. 13 and 14, with a suture attached, loaded into another modified form of the suture anchor installation tool.

Still another possible modification of the installation tool's front end 320 is shown in FIG. 16. As seen in FIG. 16, suture anchor 505 is shown in engagement with the front end 720 of a cannula 710 of an installation tool; only the front end 720 of the cannula is shown, inasmuch as the remainder of the cannula is identical to the rear end of cannula 310 already described and illustrated. It will be appreciated that the unshown portion of cannula 710 mates with an installation tool handle 305 such as that already described and illustrated, in the manner already described and illustrated.

The front end 720 of cannula 710 is characterized by an internal bore 724 which has a diameter slightly greater than the suture anchor's coupling member 510. Cannula 710 terminates in a front end surface 730, and has one or more radially intruding crimps 750 which serve as a stop for engaging the upper surface of the cannula and preventing it from riding up into the interior of the cannula. Crimps 750 are positioned so that a portion of the suture anchor's coupling member can be received within the cannula's bore 724, with the suture anchor's bore 535 still being completely exposed, as shown. A slot 735 terminating in a rear surface 740 is provided to accommodate the suture anchor's barb 515.

Except for the foregoing differences in construction, and except for the foregoing differences in the way coupling member 515 mates with cannula 710, it will be appreciated that suture anchor 505 and cannula 710 operate in substantially the same manner as suture anchor 105 and cannula 310 previously described.

Figure 17:
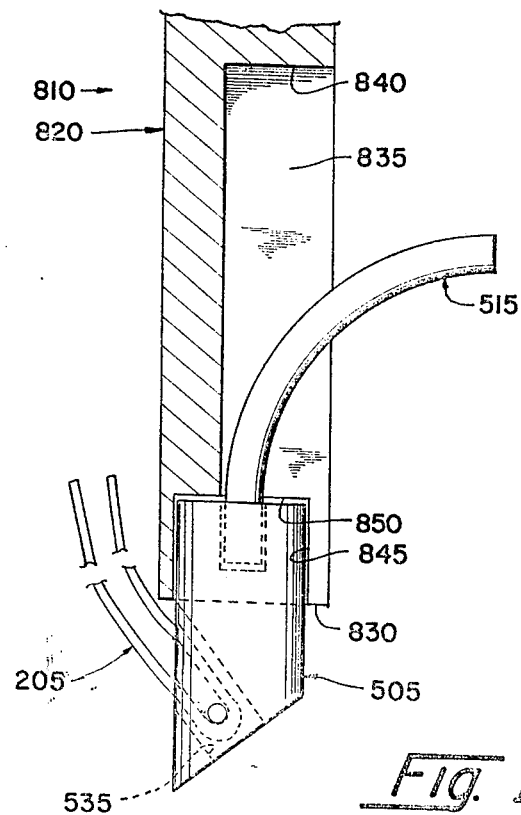
FIG. 17 is a partial side view in elevation showing the suture anchor of FIGS. 13 and 14, with a suture attached, loaded into still another modified form of the suture anchor installation tool.

Still another possible modification of the installation tool's front end 320 is shown in FIG. 17. As seen in FIG. 17, suture anchor 505 is shown in engagement with the front end 820 of a rod 810 of an installation tool; only the front end 820 of rod 810 is shown, inasmuch as the remainder of the rod is substantially identical to the rear end of cannula 310 already described and illustrated. It will be appreciated that the unshown portion of rod 810 mates with an installation tool handle 305 such as that already described and illustrated, in the manner already described and illustrated.

The front end 820 of rod 810 is characterized by a solid body having a front end surface 830. A blind hole 845 opens on front end surface 830 and terminates in a flat surface 850. Blind hole 845 has a diameter slightly greater than the suture anchor's coupling member 510, whereby a portion of the suture anchor's coupling member can be received within the rod's blind hole 845, with the suture anchor's bore 835 still being completely exposed, as shown. A slot 835, communicating with blind hole 845 and terminating in a rear surface 840, is provided to accommodate the suture anchor's barb 515.

Except for the foregoing differences in construction, and except for the foregoing differences in the way coupling member 515 mates with rod 810, it will be appreciated that suture anchor 505 and rod 810 operate in substantially the same manner as the suture anchor 105 and cannula 310 previously described.

It is also anticipated that one might increase the height of dimples 381B and make them out of a flexible material, whereby the suture will push over and then slip past the deflected dimples as it plays out of the interior of handle members 345A, 345B, rather than just slipping over the top of relatively low, rigid dimples. It is believed that such a construction might enhance holding the suture in place within the handle prior to deployment, and also provide increased tactile feedback as the suture plays out of the interior of the handle.

These and other changes of their type are believed to be obvious to those skilled in the art and within the scope of the present invention.

ADVANTAGES OF THE INVENTION

Numerous advantages are achieved by using the present invention.

For one thing, a new and improved suture anchor, and a new and improved suture anchor installation tool, are disclosed for attaching sutures to bone.

For another thing, a new and improved suture anchor is disclosed which is adapted to anchor an intermediate portion of a piece of conventional suture in bone, thereby leaving the two ends of the suture residing free outside the bone so that each of the free ends can then be used to attach the desired object or objects to the bone.

Also, a new and improved suture anchor is disclosed which is adapted to anchor an intermediate portion of a piece of conventional suture in bone, thereby leaving the two ends of the suture residing free outside the bone so that each of the free ends can then be used to attach the desired object or objects to the bone, wherein the suture anchor is adapted to have the intermediate portion of the suture attached to the suture anchor without the tying of any knots in the suture.

Still other advantages of the invention will be obvious to those skilled in the art.

What is claimed is:

1. A suture anchor for anchoring an intermediate portion of a piece of conventional suture in bone, said suture anchor comprising:
   (a) a coupling member having a first end surface and a second end surface,
   (b) at least one barb, said barb having a first end and a second end and being curved in its normal unstressed state and being capable of being elastically deformed to a substantially straight configuration, said barb being attached to said coupling member so that said second end of said barb is substantially displaced from said coupling member when said barb is in its normal unstressed state but is capable of being aligned with said coupling member when said barb is deformed to a substantially straight length, and
   (c) attachment means for attaching an intermediate portion of a piece of conventional suture to said suture anchor, said attachment means comprising a bore formed in said coupling member and a pin extending across said bore, whereby the suture can be passed around said pin so that an intermediate portion of the suture is supported by said pin and the two ends of the suture are free to attach a desired object or objects to bone.

2. A suture anchor according to claim 1 wherein said first end surface extends at an acute angle to the longitudinal axis of said coupling member, and said bore extends at an acute angle to the longitudinal axis of said coupling member.

3. A suture anchor according to claim 2 wherein said bore intersects said first end surface.

4. A suture anchor according to claim 3 wherein said bore intersects said first end surface at a right angle.

5. A suture anchor according to claim 1 wherein said coupling member comprises a first end portion including said first end surface, and a reduced second end portion including said second end surface, and a shoulder formed at the junction of said first end portion and said second end portion.

6. A suture anchor according to claim 5 wherein said bore is formed in said first end portion.

7. A suture anchor installation tool for deploying a suture anchor of the sort comprising (a) a coupling member having a first end surface and a second end surface, (b) at least one barb, said barb having a first end and a second end and being curved in its normal unstressed state and being capable of being elastically deformed to a substantially straight configuration, said barb being attached to said coupling member so that said second end of said barb is substantially displaced from said coupling member when said barb is in its normal unstressed state but is capable of being aligned with said coupling member when said barb is deformed to a substantially straight length, and (c) attachment means for attaching a portion of a piece of conventional suture to said suture anchor, said suture anchor installation tool comprising a first body portion and a second body portion, said first body portion having a first end and a second end, said first end of said first body portion being hollow and having a slot extending from said first end of said first body portion towards said second end of said first body portion, said first end of said first body portion being sized to accommodate a portion of said coupling member, and said slot being sized to accommodate said barb of said suture anchor, and said second body portion having a first end and a second end, said second body portion having a hollow interior and an opening leading to said hollow interior, said hollow interior being sized to accommodate an intermediate portion of a suture attached to the suture anchor, and said opening being sized to accommodate four widths of said suture, with said second end of said first body portion being joined to said first end of said second body portion, whereby said suture anchor may be attached to said first end of said first body portion by fitting a portion of said coupling member into said first end of said first body portion and by fitting said barb of said suture anchor into said slot so that said barb extends outward and away from said first end of said first body portion, through said slot, and an intermediate portion of said suture may be stored within said hollow interior.

8. A suture anchor installation tool according to claim 7 wherein said hollow interior comprises a plurality of elongated parallel chambers.

9. A suture anchor installation tool according to claim 7 wherein said second body portion comprises releasable holding means for releasably holding a suture length in position within said hollow interior.

10. A suture anchor installation tool according to claim 9 wherein said releasable holding means comprises a plurality of rigid dimples projecting into said hollow interior.

11. A suture anchor installation tool according to claim 9 wherein said releasable holding means comprises a plurality of deflectable fingers projecting into said hollow interior.

12. A suture anchor installation tool according to claim 7 wherein said second body portion comprises a pair of grooves formed in its outer surface and sized to accomodate a pair of curved surgical needles.

13. A suture anchor installation tool according to claim 7 further including a second opening in said second body portion leading to said hollow interior.

14. A suture anchor installation tool according to claim 7 wherein at least a portion of said second body portion is formed out of a transparent material.

15. A suture anchor installation tool according to claim 7 further including means for determining the orientation of said barb relative to said second body portion when said suture anchor is attached to said first end of said first body portion.

16. A suture anchor installation tool according to claim 15 wherein the shape of said second body portion is arranged so as to indicate the orientation of said barb relative to said second body portion.

17. A suture anchor installation tool according to claim 7 wherein said tool further comprises stop means for regulating penetration of said tool into a bone.

18. A suture anchor installation tool according to claim 7 wherein said hollow interior comprises at least two elongated parallel chambers.

19. A suture anchor installation tool according to claim 7 wherein said second body portion comprises a pair of grooves formed in its outer surface for accomodating a pair of curved surgical needles, and means for holding said needles in said grooves.

20. A suture anchor installation tool according to claim 19 wherein said grooves are formed so as to form an interference fit with said curved surgical needles.

21. A suture anchor installation tool according to claim 7 wherein said second body portion comprises releasable holding means for releasably holding a suture length in position within said hollow interior.

22. A suture anchor installation tool according to claim 7 wherein said second body portion comprises releasable holding means for releasably holding a suture length in position within said hollow interior and permitting said suture length to be pulled out of said second body portion under axial tension.

23. A suture anchor system for anchoring an intermediate portion of a piece of conventional suture in bone, said system comprising:

a suture anchor comprising:
(a) a coupling member having a first end surface and a second end surface,
(b) at least one barb, said barb having a first end and a second end and being curved in its normal unstressed state and being capable of being elastically deformed to a substantially straight configuration, said barb being attached to said coupling member so that said second end of said barb is substantially displaced from said coupling member when said barb is in its normal unstressed state but is capable of being aligned with said coupling member when said barb is deformed to a substantially straight length, and
(c) attachment means for attaching an intermediate portion of a piece of conventional suture to said suture anchor, said attachment means comprising a bore formed in said coupling member and a pin extending across said bore, whereby the suture can be passed around said pin so that an intermediate portion of the suture is supported by said pin and the two ends of the suture are free to attach a desired object or objects to bone;

a suture anchor installation tool comprising a first body portion and a second body portion, said first body portion having a first end and a second end, said first end of said first body portion being hollow and having a slot extending from said first end of said first body portion towards said second end of said first body portion, said first end of said first body portion being sized to accommodate a portion of said coupling member, and said slot being sized to accommodate said barb of said suture anchor, and said second body portion having a first end and a second end, said second body portion having a hollow interior and an opening leading to said hollow interior, said hollow interior being sized to accommodate an intermediate portion of a suture attached to the suture anchor, and said opening being sized to accommodate four widths of said suture, with said second end of said first body portion being joined to said first end of said second body portion, whereby said suture anchor may be attached to said first end of said first body portion by fitting a portion of said coupling member into said first end of said first body portion and by fitting said barb of said suture anchor into said slot so that said barb extends outward and away from said first end of said first body portion, through said slot, with said shoulder of said suture anchor engaging said first end of said first body portion; and a suture comprising first and second ends and first and second intermediate portions disposed between said first and second ends, said suture being attached to said suture anchor by passing said first intermediate portion of said suture around the suture anchor's pin and having said second intermediate portion of said suture stored inside said hollow interior of the second body portion.

24. A suture anchor system according to claim 23 wherein said suture anchor's first end surface extends at an acute angle to the longitudinal axis of said coupling member, and said bore extends at an acute angle to the longitudinal axis of said coupling member.

25. A suture anchor system according to claim 24 wherein said suture anchor's bore intersects said first end surface.

26. A suture anchor system according to claim 25 wherein said bore intersects said first end surface at a right angle.

27. A suture anchor system according to claim 23 wherein said coupling member comprises a first end portion including said first end surface, and a reduced second end portion including said second end surface, and a shoulder formed at the junction of said first end portion and said second end portion, and further wherein said first body portion of said suture anchor installation tool is sized to accommodate said second end portion of said suture anchor but not said first end portion of said suture anchor.

28. A suture anchor system according to claim 23 wherein said suture anchor's bore is formed in said first end portion of said suture anchor.

29. A suture anchor system according to claim 23 wherein said hollow interior of said suture anchor installation tool comprises a plurality of elongated parallel chambers.

30. A suture anchor system according to claim 23 wherein said second body portion of said suture anchor installation tool comprises releasable holding means for releasably holding a suture length in position within said hollow interior.

31. A suture anchor system according to claim 30 wherein said releasable holding means comprises a plurality of rigid dimples projecting into said hollow interior.

32. A suture anchor system according to claim 30 wherein said releasable holding means comprises a plurality of deflectable fingers projecting into said hollow interior.

33. A suture anchor system according to claim 23 wherein said system further comprises a pair of curved surgical needles attached to said first and second ends of said suture, and further wherein said second body portion of said suture anchor installation tool comprises a pair of grooves formed in its outer surface and sized to accommodate a pair of surgical needles.

34. A suture anchor system according to claim 23 further including a second opening in said second body portion leading to said hollow interior.

35. A suture anchor system according to claim 23 wherein at least a portion of said second body portion is formed out of transparent material.

36. A suture anchor system according to claim 23 further including means for determining the orientation of said barb relative to said second body portion when said suture anchor is attached to said first end of said first body portion.

37. A suture anchor system according to claim 36 wherein the shape of said second body portion is arranged so as to indicate the orientation of said barb relative to said second body portion.

38. A suture anchor system according to claim 23 wherein said tool further comprises stop means for regulating penetration of said tool into a bone.

39. A suture anchor system according to claim 23 wherein said hollow interior of said suture anchor installation tool comprises at least two elongated parallel chambers.

40. A suture anchor system according to claim 23 wherein said system further comprises a pair of curved surgical needles attached to said first and second ends of said suture, and further wherein said second body portion of said suture anchor installation tool comprises a pair of grooves formed in its outer surface for accommodating a pair of surgical needles, and means for holding said needles in said grooves.

41. A suture anchor system according to claim 40 wherein said grooves are formed so as to form an interference fit with said curved surgical needles.

42. A suture anchor system according to claim 23 wherein said second body portion comprises releasable holding means for releasably holding a suture length in position within said hollow interior.

43. A suture anchor system according to claim 23 wherein said second body portion comprises releasable holding means for releasably holding a suture length in position within said hollow interior and permitting said suture length to be pulled out of said second body portion under axial tension.

44. A method for anchoring an intermediate portion of a piece of conventional suture in bone, said method comprising the steps of:
(1) providing a suture anchor system comprising:
a suture anchor comprising:
(a) a coupling member having a first end surface and a second end surface,
(b) at least one barb, said barb having a first end and a second end and being curved in its normal unstressed state and being capable of being elastically deformed to a substantially straight configuration, said barb being attached to said coupling member so that said second end of said barb is substantially displaced from said coupling member when said barb is in its normal unstressed state but is capable of being aligned with said coupling member when said barb is deformed to a substantially straight length, and (c) attachment means for attaching an intermediate portion of a piece of conventional suture to said suture anchor, said attachment means comprising a bore formed in said coupling member and a pin extending across said bore, whereby the suture can be passed around said pin so that an intermediate portion of the suture is supported by said pin and the two ends of the suture are free to attach a desired object or objects to bone;

a suture anchor installation tool comprising a first body portion and a second body portion, said first body portion having a first end and a second end, said first end of said first body portion being hollow and having a slot extending from said first end of said first body portion towards said second end of said first body portion, said first end of said first body portion being sized to accommodate a portion of said coupling member, and said slot being sized to accommodate said barb of said suture anchor, and said second body portion having a first end and a second end, said second body portion having a hollow interior and an opening leading to said hollow interior, said hollow interior being sized to accommodate an intermediate portion of a suture attached to the suture anchor, and said opening being sized to accommodate four widths of a suture, with said second end of said first body portion being joined to said first end of said second body portion, whereby said suture anchor may be attached to said first end of said first body portion by fitting a portion of said coupling member into said first end of said first body portion and by fitting said barb of said suture anchor into said slot so that said barb extends outward and away from said first end of said first body portion, through said slot, with said shoulder of said suture anchor engaging said first end of said first body portion; and a suture comprising first and second ends and first and second intermediate portions disposed between said first and second ends, said suture being attached to said suture anchor by passing said first intermediate portion of said suture around said suture anchor's pin and having said second intermediate portion of said suture stored inside said hollow interior of the second body portion;

(2) forming a hole in the bone which is to have said suture attached to it;
(3) inserting said first end of said installation tool and said suture anchor into said hole in said bone; and
(4) withdrawing said installation tool from said hole in said bone, leaving said suture anchor disposed in said hole and said suture attached to said bone.

45. A suture anchor for anchoring a piece of conventional suture in bone, said suture anchor comprising:
(a) a coupling member,
(b) at least one barb, said barb having a first end and a second end and being curved in its normal unstressed state and being capable of being elastically deformed to a substantially straight configuration, said barb being attached to said coupling member so that said second end of said barb is substantially displaced from said coupling member when said barb is in its normal unstressed state but is capable of being aligned with said coupling member when said barb is deformed to a substantially straight length, and
(c) attachment means for attaching a portion of a piece of conventional suture to said suture anchor, said attachment means comprising a bore formed in said coupling member and suture holding means in said bore.

46. A suture anchor according to claim 45 wherein said suture holding means comprises means projecting into said bore.

47. A suture anchor according to claim 45 wherein said suture holding means comprises means extending transversely of said bore.

48. A suture anchor according to claim 45 wherein said suture holding means comprises a pin extending across said bore.

49. A suture anchor installation tool for deploying a suture anchor of the sort comprising (a) a coupling member, (b) at least one barb, said barb having a first end and a second end and being curved in its normal unstressed state and being capable of being elastically deformed to a substantially straight configuration, said barb being attached to said coupling member so that said second end of said barb is substantially displaced from said coupling member when said barb is in its normal unstressed state but is capable of being aligned with said coupling member when said barb is deformed to a substantially straight length, and (c) attachment means for attaching a piece of conventional suture to said suture anchor, said suture anchor installation tool comprising a first body portion and a second body portion, said first body portion having a first end and a second end, said first end of said first body portion being hollow and having a slot extending from said first end of said first body portion towards said second end of said first body portion, said first end of said first body portion being sized to accommodate a portion of said coupling member, and said slot being sized to accommodate said barb of said suture anchor, and said second body portion having a first end and a second end, said second body portion having a hollow interior and an opening leading to said hollow interior, said hollow interior being sized to accommodate an intermediate portion of a suture attached to the suture anchor, and said opening being sized to accommodate at least two cross-sections of said suture, with said second end of said first body portion being joined to said first end of said second body portion, whereby said suture anchor may be attached to said first end of said first body portion by fitting a portion of said coupling member into said first end of said first body portion and by fitting said barb of said suture anchor into said slot so that said barb extends outward and away from said first end of said first body portion, through said slot, and an intermediate portion of said suture may be stored within said hollow interior.

50. A suture anchor system for anchoring a piece of conventional suture in bone, said system comprising:
- a suture anchor comprising:
  - (a) a coupling member;
  - (b) at least one barb, said barb having a first end and a second end and being curved in its normal unstressed state and being capable of being elastically deformed to a substantially straight configuration, said barb being attached to said coupling member so that said second end of said barb is substantially displaced from said coupling member when said barb is in its normal unstressed state but is capable of being aligned with said coupling member when said barb is deformed to a substantially straight length, and
  - (c) attachment means for attaching a portion of a piece of conventional suture to said suture anchor, said attachment means comprising a bore formed in said coupling member and suture holding means for holding a suture in said bore;
- a suture anchor installation tool comprising a first body portion and a second body portion,
  - said first body portion having a first end and a second end, said first end of said first body portion being hollow and having a slot extending from said first end of said first body portion towards said second end of said first body portion, said first end of said first body portion being sized to accommodate a portion of said coupling member, and said slot being sized to accommodate said barb of said suture anchor, and
  - said second body portion having a first end and a second end, said second body portion having a hollow interior and an opening leading to said hollow interior, said hollow interior being sized to accommodate an intermediate portion of a suture attached to the suture anchor, and said opening being sized to accommodate at least two cross-sections of said suture, with said second end of said first body portion being joined to said first end of said second body portion, whereby said suture anchor may be attached to said first end of said first body portion by fitting a portion of said coupling member into said first end of said first body portion and by fitting said barb of said suture anchor into said slot so that said barb extends outward and away from said first end of said first body portion, through said slot; and
- a suture comprising first and second ends and first and second intermediate portions disposed between said first and second ends, said first intermediate portion of said suture being attached to said suture anchor by said suture holding means, and said second intermediate portion of said suture being stored inside said hollow interior of the second body portion.

51. A suture anchor system according to claim 50 wherein said suture holding means comprises means projecting into said bore.

52. A suture anchor system according to claim 50 wherein said suture holding means comprises means extending transversely of said bore.

53. A suture anchor system according to claim 50 wherein said suture holding means comprises a pin extending across said bore.

54. A suture anchor system according to claim 50 further including a first needle attached to said first end of said suture, and a second needle attached to said second end of said suture.

55. A method for anchoring a piece of conventional suture in bone, said method comprising the steps of:
(1) providing a suture anchor system comprising:
- a suture anchor comprising:
  - (a) a coupling member;
  - (b) at least one barb, said barb having a first end and a second end and being curved in its normal unstressed state and being capable of being elastically deformed to a substantially straight configuration, said barb being attached to said coupling member so that said second end of said barb is substantially displaced from said coupling member when said barb is in its normal unstressed state but is capable of being aligned with said coupling member when said barb is deformed to a substantially straight length, and
  - (c) attachment means for attaching a portion of a piece of conventional suture to said suture anchor, said attachment means comprising a bore formed in said coupling member and suture holding means disposed in said bore;
- a suture anchor installation tool comprising a first body portion and a second body portion,
  - said first body portion having a first end and a second end, said first end of said first body portion being hollow and having a slot extending from said first end of said first body portion towards said second end of said first body portion, said first end of said first body portion being sized to accommodate a portion of said coupling member, and said slot being sized to accommodate said barb of said suture anchor, and
  - said second body portion having a first end and a second end, said second body portion having a hollow interior and an opening leading to said hollow interior, said hollow interior being sized to accommodate an intermediate portion of a suture attached to the suture anchor, and said opening being sized to accommodate at least two cross-sections of a suture, with said second end of said first body portion being joined to said first end of said second body portion, whereby said suture anchor may be attached to said first end of said first body portion by fitting a portion of said coupling member into said first end of said first body portion and by fitting said barb of said suture anchor into said slot so that said barb extends outward and away from said first end of said first body portion, through said slot; and
- a suture comprising first and second ends and first and second intermediate portions disposed between said first and second ends, said first intermediate portion of said suture being attached to said suture anchor by said suture holding means, and said second intermediate portion of said suture being stored inside said hollow interior of the second body portion;
(2) forming a hole in the bone which is to have said suture attached top it;
(3) inserting said first end of said installation tool and said suture anchor into said hole in said bone; and
(4) withdrawing said installation tool from said hole in said bone, leaving said suture anchor disposed in said hole and said suture attached to said bone.

* * * * *

UNITED STATES PATENT AND TRADEMARK OFFICE
CERTIFICATE OF CORRECTION

PATENT NO. : 4,946,468

DATED : August 7, 1990

INVENTOR(S) : Lehmann K. Li

It is certified that error appears in the above-identified patent and that said Letters Patent is hereby corrected as shown below:

Claim 50, col. 19, line 6, the semi-colon after the word "member" should be changed to a comma;

Claim 55, col. 20, line 7, the semi-colon after the word "member" should be changed to a comma; and Claim 55, col. 20, line 62, the word "top" should be changed to the word -- to --.

Signed and Sealed this

Twenty-eighth Day of July, 1992

Attest:

DOUGLAS B. COMER

*Attesting Officer*     *Acting Commissioner of Patents and Trademarks*